US012569291B2

(12) United States Patent
Ullrich et al.

(10) Patent No.: US 12,569,291 B2
(45) Date of Patent: Mar. 10, 2026

(54) ELECTROSURGICAL RESECTOR TOOL

(71) Applicant: Creo Medical Limited, Chepstow (GB)

(72) Inventors: George Christian Ullrich, Bethesda (GB); Christopher Paul Hancock, Chepstow (GB)

(73) Assignee: Creo Medical Limited, Chepstow (GB)

( * ) Notice: Subject to any disclaimer, the term of this patent is extended or adjusted under 35 U.S.C. 154(b) by 430 days.

(21) Appl. No.: 18/025,807

(22) PCT Filed: Oct. 6, 2021

(86) PCT No.: PCT/EP2021/077621
§ 371 (c)(1),
(2) Date: Mar. 10, 2023

(87) PCT Pub. No.: WO2022/100934
PCT Pub. Date: May 19, 2022

(65) Prior Publication Data
US 2023/0355296 A1 Nov. 9, 2023

(30) Foreign Application Priority Data

Nov. 12, 2020 (GB) ...................................... 2017867

(51) Int. Cl.
*A61B 18/12* (2006.01)
*A61B 18/14* (2006.01)
(Continued)

(52) U.S. Cl.
CPC .............................. *A61B 18/1445* (2013.01); *A61B 2018/00077* (2013.01); *A61B 2018/00982* (2013.01); *A61B 2018/147* (2013.01)

(58) Field of Classification Search
CPC . A61B 18/1445; A61B 18/1482; A61B 18/16; A61B 18/1815; A61B 2018/00196;
(Continued)

(56) References Cited

U.S. PATENT DOCUMENTS 5,275,615 A * 1/1994 Rose ...................... A61B 17/29
606/208
5,951,549 A 9/1999 Richardson et al.
(Continued)

FOREIGN PATENT DOCUMENTS

GB 2550375 A 11/2017
GB 2567480 A 4/2019
JP 2019516426 A 6/2019

OTHER PUBLICATIONS

Examination Report Under Section 17(5), issued by the United Kingdom Intellectual Property Office in corresponding United Kingdom Application No. GB2017867.9, dated May 7, 2021.
(Continued)

*Primary Examiner* — Daniel W Fowler
(74) *Attorney, Agent, or Firm* — ArentFox Schiff LLP

(57) ABSTRACT
An electrosurgical resector tool comprising an energy conveying structure for carrying radiofrequency (RF) electromagnetic (EM) energy and microwave EM energy having an instrument tip mounted at a distal end thereof. The instrument tip comprises first and second jaws. The second jaw is movable between a closed position and an open position, in which the second jaw is spaced from the first by a gap for receiving biological tissue. The first and second jaws respectively comprise first and second pairs of electrodes that are electrically isolated. The first and second pairs of electrodes are respectively coupled to the energy conveying structure, such that each pair is operable as active and return electrodes for delivering RF EM energy carried by the energy conveying structure. The first and second pairs of electrodes are operable as a microwave field emitting structure for emitting microwave EM energy carried by the energy conveying structure.

16 Claims, 6 Drawing Sheets

(51) Int. Cl.
　　*A61B 18/18*　　　(2006.01)
　　*A61B 18/00*　　　(2006.01)
(58) Field of Classification Search
　　CPC ........... A61B 2018/00589; A61B 2018/00607;
　　　　　　A61B 2018/00982; A61B 2018/147;
　　　　　　　　　　A61B 2018/162
　　See application file for complete search history.

(56)　　　　　　References Cited

U.S. PATENT DOCUMENTS

| | | | |
|---|---|---|---|
| 6,391,029 B1 | 5/2002 | Hooven et al. | |
| 6,447,511 B1 * | 9/2002 | Slater ................. | A61B 18/1445 |
| | | | 606/49 |
| 9,381,066 B2 | 7/2016 | Hancock | |

| | | | |
|---|---|---|---|
| 2008/0027427 A1 * | 1/2008 | Falkenstein ........ | A61B 18/1445 |
| | | | 606/45 |
| 2012/0289958 A1 | 11/2012 | Falkenstein et al. | |
| 2016/0331455 A1 * | 11/2016 | Hancock ............ | A61B 18/1815 |
| 2019/0167342 A1 | 6/2019 | Hancock et al. | |
| 2020/0253664 A1 | 8/2020 | Hancock et al. | |

OTHER PUBLICATIONS

International Seach Report, issued by the International Searching Authority in corresponding International Application No. PCT/EP2021/077621, mailed Feb. 4, 2022.

Written Opinion of the International Searching Authority, issued by the International Searching Authority in corresponding International Patent Application No. PCT/EP2021/077621, mailed Feb. 4, 2022.

* cited by examiner

900

902                          904

908      910          906  912      916          914

1000

1002                          1004

1008      1010    1006      1012  1016      1014
                        1018

ELECTROSURGICAL RESECTOR TOOL

CROSS-REFERENCE TO RELATED APPLICATIONS

The present Application for Patent is a National Stage Entry of International Application No. PCT/EP2021/077621, filed Oct. 6, 2021, which claims priority to United Kingdom Patent Application No. 2017867.9, filed Nov. 12, 2020. The disclosures of the priority documents are incorporated in their entirety by reference herein.

FIELD OF THE INVENTION

The invention relates to an electrosurgical resector tool for cutting, coagulating and ablating biological tissue. In particular the invention relates to an electrosurgical resector tool capable of delivering radiofrequency (RF) energy and/or microwave frequency energy for cutting biological tissue, haemostasis (i.e. sealing broken blood vessels by promoting coagulation of blood) and tissue ablation.

BACKGROUND TO THE INVENTION

Surgical resection is a means of removing sections of organs from within the human or animal body. The organs may be highly vascular. When tissue is cut (i.e. divided or transected), small blood vessels may be damaged or ruptured. Initial bleeding is followed by a coagulation cascade where the blood is turned into a clot in an attempt to plug the bleed. During an operation it is desirable for a patient to lose as little blood as possible, so various devices have been developed in an attempt to provide bleeding-free cutting. For endoscopic procedures, it is also undesirable for a bleed to occur and not to be dealt with expediently, since the flow of blood may obscure the operator's vision.

Instead of a sharp blade, it is known to use RF energy to cut biological tissue. The method of cutting using RF energy operates using the principle that as an electric current passes through a tissue matrix (aided by the ionic cell contents), the impedance to electron flow across the tissue generates heat. When a pure sine wave is applied to the tissue matrix, enough heat is generated within the cells to vaporize the water content of the tissue. There is thus a huge rise in the internal cell pressure that cannot be controlled by the cell membrane, resulting in rupture of the cell. When this occurs over a large area, it can be seen that the tissue is transected. The above procedure works elegantly in lean tissue, but it is less efficient in fatty tissue because there are fewer ionic constituents to aid the passage of electrons. This means that the energy required to vaporize the contents of the cells is much greater, since the latent heat of vaporization of fat is much greater than the latent heat of vaporization of water.

RF coagulation operates by applying a less efficient waveform to the tissue, whereby instead of being vaporized, the cell contents are heated to around 65° C., drying out the tissue by desiccation and denaturing the proteins in the vessel walls. This denaturing acts as a stimulus to the coagulation cascade, so clotting is enhanced. At the same time the collagen in the wall is denatured, turning from a rod-shaped to a coil-shaped molecule, causing the vessel to contract and reduce in size, giving the clot an anchor point, and a smaller area to be plugged. However, RF coagulation is less efficient when fatty tissue is present because the electrical effect is diminished. It can thus be very difficult to seal fatty bleeders. Instead of having clean white margins, the tissue has a blackened burned appearance.

Tissue ablation using microwave electromagnetic (EM) energy is based on the fact that biological tissue is largely composed of water. Human soft organ tissue is typically between 70% and 80% water content. Water molecules have a permanent electric dipole moment, meaning that a charge imbalance exists across the molecule. This charge imbalance causes the molecules to move in response to the forces generated by application of a time varying electric field as the molecules rotate to align their electric dipole moment with the polarity of the applied field. At microwave frequencies, rapid molecular oscillations result in frictional heating and consequential dissipation of the field energy in the form of heat. This is known as dielectric heating. This principle is harnessed in microwave ablation therapies, where water molecules in target tissue are rapidly heated by application of a localised electromagnetic field at microwave frequencies, resulting in tissue coagulation and cell death.

SUMMARY OF THE INVENTION

At its most general the present invention provides an electrosurgical resector tool having an energy delivery structure that provides a plurality of operational modalities that facilitate biological tissue cutting and sealing using radiofrequency (RF) electromagnetic energy and/or microwave EM energy. In particular, the invention relates to combined actuation and energy delivery mechanisms that are compact enough to enable the tool to be insertable through an instrument channel of a surgical scoping device, such as an endoscope, gastroscope or bronchoscope. The device could also be used to perform laparoscopic or open surgery, i.e. the bloodless resection of a liver lobe with the abdominal cavity open.

The invention represents a development to the electrosurgical resector tool concept discussed in GB2567480. The electrosurgical resector tool of the invention comprises a pair of jaws, each of which has a respective pair of electrodes. This may enable the electrosurgical resector tool to be operated according to three complimentary modalities: (i) a gliding RF-based cut when the jaws are closed, (ii) a scissor-type cut performed on tissue grasped between the jaws using a combination of RF energy and applied pressure, and (iii) a coagulation or vessel sealing operation performed on tissue grasped between the jaws using a combination of microwave energy and applied pressure. The inventors have found that, by providing a pair of electrodes on each jaw, it is possible to improve the tool's ability to cut and coagulate tissue using EM energy. In particular, such an arrangement of electrodes may enable multiple RF fields to be established across the jaws, which may result in a smoother, more uniform cut. Similarly, such an electrode configuration may lead to more effective tissue coagulation and ablation using microwave energy, by enabling emitting a more uniform microwave field and/or by emitting multiple microwave fields across the jaws.

According to the invention, there is provided an electrosurgical resector tool comprising: an energy conveying structure for carrying radiofrequency (RF) electromagnetic (EM) energy and microwave EM energy, the energy conveying structure comprising a coaxial transmission line having an inner conductor separated from an outer conductor by a dielectric material; an instrument tip mounted at a distal end of the energy conveying structure, wherein the instrument tip comprises a first jaw and a second jaw, wherein the second jaw is movable relative to the first jaw between a closed position in which the first jaw and second jaw lie alongside each other, and an open position in which the second jaw is spaced from the first jaw by a gap for receiving biological tissue; wherein the first jaw comprises a first pair of electrodes that are electrically isolated from one another; wherein the second jaw comprises a second pair of electrodes that are electrically isolated from one another; wherein the first pair of electrodes is coupled to the energy conveying structure, such that the first pair of electrodes is operable as active and return electrodes for delivering RF EM energy carried by the energy conveying structure; wherein the second pair of electrodes is coupled to the energy conveying structure, such that the second pair of electrodes is operable as active and return electrodes for delivering RF EM energy carried by the energy conveying structure; and wherein the first and second pairs of electrodes are operable as a microwave field emitting structure for emitting microwave EM energy carried by the energy conveying structure.

The energy conveying structure may be disposed in a lumen of a shaft (or outer sheath), such that the instrument tip protrudes from a distal end of the shaft. The shaft may be any suitable shaft through which the coaxial transmission line can be inserted. The shaft may be flexible, e.g. suitable for bending or other steering to reach the treatment site. A flexible shaft may enable the device to be usable in a surgical scoping device such as an endoscope. In other examples, the shaft may be rigid, e.g. for use in open surgery or with a laparoscope.

The coaxial transmission line may be adapted to convey both the RF EM energy and the microwave EM energy. Alternatively, the energy conveying structure may comprise different routes for the RF EM energy and microwave EM energy. For example, the microwave EM energy may be delivered through the coaxial transmission line, whereas the RF EM energy can be delivered via twisted pair wires or the like. The coaxial transmission line may be in the form of a flexible coaxial cable.

As an example, the inner conductor may be electrically connected to a first electrode of the first pair of electrodes and to a first electrode of the second pair of electrodes, and the outer conductor may be electrically connected to a second electrode of the first pair of electrodes and to a second electrode of the second pair of electrodes. With such an arrangement, RF EM and/or microwave EM may be conveyed by the coaxial transmission line to the first and second pairs of electrodes.

The first jaw and the second jaw are mounted at the distal end of the energy conveying structure such that they are movable relative to one another between the open and closed positions. Various types of relative movement between the jaws may be used. The relative movement between the first jaw and the second jaw may comprise rotational and/or translational movement. At least one of the first jaw and the second jaw may be movably mounted relative to the distal end of the energy conveying structure, to enable relative movement between the first and second jaws. In some cases, only one of the first and second jaws may be movably mounted relative to the distal end of the energy conveying structure, whilst in other cases both the first and second jaws may be movably mounted relative to the distal end of the energy conveying structure.

As an example, the first jaw and second jaw may be pivotable relative to one another, e.g. such that an opening angle between the first jaw and the second jaw can be adjusted. This example may resemble a scissor-type closure. The first jaw and/or the second jaw may be pivotally mounted at the distal end of the energy conveying structure.

In another example, it may be beneficial for the gap between the first and second jaws to be uniform once tissue is grasped therebetween, e.g. to ensure that the energy supplied is uniform along the length of the jaws. In this example, the first jaw and the second jaw may be configured to remain parallel when they are moved relative to one another. For instance, the first jaw and the second jaw may be parallel when the jaws are in the open position, and the first and second jaws may remain parallel when sliding past one another to the closed position.

The first jaw may comprise a first blade element, and the second jaw may comprise a second blade element. Then, when the jaws are in the closed position, the first blade element may lie alongside the second blade element, and when the jaws are in the open position, there may be a gap between the first blade element and the second blade element for receiving biological tissue.

The first blade element and the second blade element may be configured to cut tissue disposed in the gap between the first and second jaws when the first and second jaws are moved from the open position to the closed position. Thus, the first blade element and the second blade element may each include a cutting (e.g. sharp) edge that is arranged for cutting tissue. A cutting interface may be defined between the first jaw and the second jaw, corresponding to a region in which tissue between the jaws is cut when the jaws are closed.

The first blade element and the second blade element may be arranged to slide past one another when the first and second jaws are moved between the open position and closed position, e.g. to effect mechanical cutting of tissue through application of a shearing force. Thus, cutting effected by the first and second blade elements may resemble a scissors-type cutting mechanism.

The first and/or second blade element may include one or more serrations (e.g. teeth). The serrations may facilitate gripping and cutting tissue located in the gap between the jaws.

The electrosurgical resector tool may comprise an actuator for controlling movement of the second jaw relative to the first jaw. The actuator may comprise any suitable type of actuator for controlling relative movement between the jaws. As an example, the actuator may comprise a control rod that extends along the energy conveying structure (e.g. inside the shaft), and that is movable along its length to control the position of one or both of the jaws. The control rod may have an attachment feature engaged with one or both of the first and second jaws, whereby longitudinal movement of the control rod causes movement of the second jaw relative to the first jaw. The attachment feature may be a hook or any suitable engagement for transmitting push and pull forces to the one or both of the jaws.

The first pair of electrodes is disposed on the first jaw, with a first electrode in the first pair acting as an active electrode for the RF EM energy, and a second electrode in the first pair acting as a return electrode for the RF EM energy. In this manner, RF EM energy carried by the energy conveying structure can be delivered to tissue via the first pair of electrodes. The first pair of electrodes can establish a first RF cutting field with the RF EM energy from the energy conveying structure, in order to cut target tissue. The first pair of electrodes may be exposed on a surface of the first jaw, so that they can contact target tissue to deliver RF EM energy into the target tissue.

The second pair of electrodes is disposed on the second jaw, with a first electrode in the second pair acting as an active electrode for the RF EM energy, and a second electrode in the second pair acting as a return electrode for the RF EM energy. In this manner, RF EM energy carried by the energy conveying structure can further be delivered to tissue via the second pair of electrodes. The second pair of electrodes can establish a second RF cutting field with the RF EM energy from the energy conveying structure, in order to cut target tissue. The second pair of electrodes may be exposed on a surface of the second jaw, so that they can contact target tissue to deliver RF EM energy into the target tissue.

Thus, when RF EM energy is conveyed by the energy conveying structure, a first RF cutting field is established by the first pair of electrodes, and a second RF cutting field is established by the second pair of electrodes. In other words, a respective RF cutting field may be established at each jaw. Furthermore, an RF cutting field may be established between the jaws, e.g. between the active electrode on the first jaw and the return electrode on the second jaw (and vice versa). Thus, RF cutting may occur at each jaw, as well as between the jaws. This may enable RF cutting to be performed across a larger region of tissue, as well as enable more uniform RF cutting to be performed.

Moreover, the first and second pairs of electrodes serve to define a microwave field emitting structure for emitting (or radiating) microwave EM energy from the energy conveying structure. Thus, microwave EM energy carried by the energy conveying structure may be radiated from the first and second pairs of electrodes into target tissue, in order to coagulate and/or ablate the target tissue. Thus, the first and second pairs of electrodes may act as one or more microwave antennas for delivering microwave EM energy into tissue. The specific shape of the microwave field(s) emitted will depend on the arrangement of the pairs of electrodes in the jaws. In some examples, each pair of electrodes may act as a respective microwave field emitting structure, such that a respective microwave field is emitted at each jaw. Additionally or alternatively, electrodes in the first and second pairs may together form a microwave field emitting structure, such that a common microwave field is emitted across both jaws. Using pairs of electrodes on each jaw for radiating microwave EM energy may serve to improve a uniformity and symmetry of the emitted microwave filed(s) across the jaws, which may improve an effectiveness of treatment of tissue with microwave energy.

In some embodiments, the first jaw may comprise a first planar dielectric element having an inner surface that faces towards the second jaw and an outer surface that faces away from the second jaw, and the first pair of electrodes may comprise an inner electrode and an outer electrode arranged on the inner and outer surfaces of the first planar dielectric element, respectively; and the second jaw may comprise a second planar dielectric element having an inner surface that faces towards the first jaw and an outer surface that faces away from the first jaw, and the second pair of electrodes may comprise an inner electrode and an outer electrode arranged on the inner and outer surfaces of the second planar dielectric element, respectively. Thus, each jaw may comprise an inner electrode and an outer electrode that are spaced by a respective planar dielectric element. The inner surfaces of the first and second planar dielectric elements may face towards each other, across the cutting interface between the first and second blade elements. As a result, the first pair of electrodes and the second pair of electrodes may be substantially aligned with one another in a lateral direction, when the jaws are closed. This may enable effective treatment of target tissue over a large area when the jaws are closed.

The first planar dielectric element and the second planar dielectric element may be substantially parallel to one another, e.g. a plane defined by the inner surface of the first planar dielectric element may be substantially parallel to a plane defined by the inner surface of the second planar dielectric element. The first planar dielectric element and the second planar dielectric element may each be aligned parallel to plane in which the first jaw and second jaw are movable relative to one another.

Each of the first and second planar dielectric elements may be formed by a piece of dielectric (i.e. insulating) material, such as from ceramic (e.g. alumina). Herein, reference to "planar" element may mean a flat piece of material having a thickness that is substantially less that its width and length. Each planar dielectric element may have a length dimension aligned in a longitudinal direction, a thickness dimension aligned in a lateral direction, and a width dimension orthogonal to both the length and thickness dimensions. A plane of a planar dielectric element is a plane in which the length and width dimensions lie, i.e. a plane orthogonal to the width dimension. The inner surface and outer surfaces of each planar dielectric element may be parallel to the plane of the planar dielectric element, i.e. they may be orthogonal to the width dimension. The inner and outer surfaces of each planar dielectric element may be arranged on opposite sides of the planar dielectric element, with respect to its width.

Using a planar dielectric element in each jaw, on which the electrodes are arranged, may greatly facilitate fabrication of the instrument tip. This is because the electrodes can easily be formed on their inner and outer surfaces, e.g. by depositing conductive material onto the surfaces and/or by attaching conductive elements to the surfaces. In contrast, in prior art resector tools, the jaws are typically made of a conductive material which is coated with an insulating material, with electrodes being defined by an area of the jaws where the insulating material is etched away. Defining electrodes by etching away insulating material may be a tedious and time consuming process. Additionally, the inventors have found that tissue may stick to the insulating material, rendering the instrument tip difficult to clean. Thus, using the planar dielectric elements in the jaws may facilitate manufacture of the instrument tip, as well as avoid tissue sticking to the instrument tip.

In some cases, the first planar dielectric element may define the first blade element. For example the first planar dielectric element may comprise a cutting edge that is configure to contact tissue located between the jaws and to cut the tissue when the jaws are closed. Then, the inner electrode of the first pair may be formed at or near the cutting edge of the first planar dielectric element.

Similarly, the second planar dielectric element may define the second blade element, e.g. the second planar dielectric element may comprise a cutting edge this is configured to contact and cut tissue located between the jaws. Then, the inner electrode of the second pair may be formed at or near the cutting edge of the second planar dielectric element.

Where the first planar dielectric element defines the first blade element and the second planar dielectric element defines the second blade element, the inner surface of the first planar dielectric element may be arranged to slide across the inner surface of the second planar dielectric element when the jaws are moved between the open and closed positions.

The inner electrode of the first pair of electrodes may comprise a first conductive layer formed on the inner surface of the first planar dielectric element; and the inner electrode of the second pair of electrodes may comprise a second conductive layer formed on the inner surface of the second planar dielectric element. Thus, the inner electrode of each pair may be formed by a respective layer of conductive material directly on the inner surface of the respective planar dielectric element. For example, the layer of conductive material may be deposited using any suitable deposition technique, or the layer of conductive material may be otherwise mounted to the inner surface (e.g. via an adhesive). The conductive layer for each inner electrode may be formed of any suitable conductive material, such as gold.

The first conductive layer may extend in the longitudinal direction, i.e. it may extend along all or part of a length of first planar dielectric element. Likewise, the second conductive layer may extend in the longitudinal direction, i.e. it may extend along all or part of a length of the second planar dielectric element.

Furthermore, in some cases, the outer electrode of the first pair of electrodes may comprise a third conductive layer formed on the outer surface of the first planar dielectric element; and the outer electrode of the second pair of electrodes may comprise a fourth conductive layer formed on the outer surface of the second planar dielectric element. The third and fourth conductive layers may be formed in a similar manner to the first and second conductive layers mentioned above.

Thus, no patterning and etching of an insulating layer on either of the jaws may be required in order to form the electrodes, which may greatly facilitate manufacture of the instrument tip.

The first jaw may further comprise a first conductive shell that is attached to the outer surface of the first planar dielectric element, and arranged to form at least part of the outer electrode of the first pair of electrodes; and the second jaw may further comprise a second conductive shell that is attached to the outer surface of the second planar dielectric element, and arranged to form at least part of the outer electrode of the second pair of electrodes. Thus, the outer electrode of each pair of electrodes may comprise a conductive shell mounted on the outer surface of the corresponding planar dielectric element. The first conductive shell may define an outer surface of the first jaw, whilst the second conductive shell may define an outer surface of the second jaw. Each conductive shell may thus serve the dual purposes of defining an outer electrode, as well as protecting the planar dielectric element to which it is mounted. Each conductive shell may be formed of a piece of conductive material which is attached to the outer surface of the corresponding planar dielectric element (e.g. via an adhesive and/or a mechanical fastening). Any suitable conductive material may be used for the conductive shells, such as stainless steel.

A surface area of the first conductive shell may be larger than a surface area of the inner electrode of the first pair of electrodes. For instance, the first conductive shell may be formed of a relatively thick block of conductive material that covers all or most of the outer surface of the first planar dielectric element, whilst the inner electrode may be formed as a relatively thin conductive layer on the inner surface of the first planar dielectric element. Similarly, a surface area of the second conductive shell may be larger than a surface area of the inner electrode of the second pair of electrodes. Thus, the conductive shells may serve to increase a surface area of the outer electrode in each pair relative to the inner electrode.

The inventors have found that, when a pair of spaced electrodes having different sizes are used to perform RF cutting of tissue, the tissue tends to be cut in the vicinity the smaller of the two electrodes. Accordingly, using a conductive shell with a large surface area compared to the inner electrode may ensure that RF cutting of tissue occurs near the inner electrode. This may enable a well-defined cut to be made in tissue located between the jaws using RF EM energy. In particular, this may serve to ensure that the cut produced by the RF EM energy is located at or near the cutting interface between the blade elements. Moreover, as both pairs of electrodes comprise a large outer electrode due to their respective conductive shells, each pair of electrodes may produce RF cutting of tissue that is focused on either side of the cutting interface between the blade elements. As a result, effective RF cutting of tissue located between the jaws may be ensured.

The first conductive shell and the second conductive shell may be electrically coupled to one another. In other words, the outer electrode of the first pair and the outer electrode of the second pair may be electrically connected to one another. In this manner, the first conductive shell and the second conductive shell may together act as a single large outer electrode for both pairs of electrodes. This may serve to further concentrate RF cutting around the inner electrodes, and therefore at the cutting interface between the blade elements. This may enable fine and accurate RF cutting of tissue between the jaws. The first conductive shell and the second conductive shell may be electrically coupled to one another via any suitable means. For instance, an electrical connector may be coupled between the first and second conductive shells. In some cases, the first and second conductive shells may both be coupled to a common conductor in the energy conveying structure, such that they are electrically coupled via the energy conveying structure.

The instrument tip may further comprise a base structure that connects the first conductive shell and the second conductive shell to the distal end of the energy conveying structure. In this manner, the first conductive shell may act as a support for the first jaw, via which the first jaw is mounted to the distal end of the energy conveying structure. Similarly, the second conductive shell may act as a support for the second jaw, via which the second jaw is mounted to the distal end of the energy conveying structure. This may facilitate mounting the jaws at the distal end of the energy conveying structure, as the conductive shells may be exposed at an outer surface of the jaws, and so can easily be connected to the base structure. This may also avoid having to machine any mounting holes in the planar dielectric elements, which may typically be made of brittle materials which are difficult to machine.

The base structure may be any suitable structure for supporting the jaws at the end of the energy conveying structure. The base structure may, for example comprise an arm which is secured to the distal end of the energy conveying structure at one end, and connected to the first and second jaws at another end. Such a base structure may serve to reinforce the distal end of the energy conveying structure (which may typically be flexible), and facilitate transmitting longitudinal forces to the instrument tip. The base structure may comprise a rigid material (e.g. a metal, such as stainless steel).

The first jaw and/or the second jaw may be movably connected to the base structure, to enable relative movement between the first and second jaws. For example, the first jaw and/or the second jaw may be pivotably connected to the base structure.

The base structure may include a first base part that rigidly connects the first conductive shell to the distal end of the energy conveying structure, and a second base part to which the second conductive shell is pivotably connected, such that the second jaw is pivotable relative to the second base part. Thus, the first jaw may be static, i.e. fixed relative to the base structure and thus to the distal end of the energy conveying structure, whilst the second jaw is pivotable. Accordingly, the jaws may be moved between the open and closed positions by pivoting the second jaw.

In some cases, the first base part may be a part of the first conductive shell, i.e. the first conductive shell may form part of the base structure. For instance, the first base part may be a part of the first conductive shell that extends between the first jaw and the distal end of the energy conveying structure. This may serve to ensure a rigid connection between the first jaw and the distal end of the energy conveying structure, as well as facilitate electrical connection between the outer electrode in the first pair and the energy conveying structure.

The base structure may comprise (e.g. be made of) an electrically conductive material that electrically connects the first conductive shell to a first one of the inner conductor and the outer conductor at a distal end of the coaxial transmission line. In this manner, the first conductive shell may be directly connected to a conductor of the coaxial transmission line via the base structure. For example, the first base part may comprise an electrically conductive material that electrically connects the first conductive shell to the first one of the inner conductor and the outer conductor.

Additionally or alternatively, the base structure may comprise (e.g. be made of) an electrically conductive material that electrically connects the second conductive shell to the first one of the inner conductor and the outer conductor at a distal end of the coaxial transmission line. In this manner, the second conductive shell may be directly connected to a conductor of the coaxial transmission line via the base structure. For example, the second base part may comprise an electrically conductive material that electrically connects the second conductive shell to the first one of the inner conductor and the outer conductor.

Where the first conductive shell and the second conductive shell are electrically coupled to one another, the base structure may comprise (e.g. be made of) an electrically conductive material that connects each of the first and second conductive shells to a first one of the inner conductor and the outer conductor at a distal end of the coaxial transmission line. Thus, the first conductive shell and the second conductive shell may be electrically coupled via the base structure.

The base structure may define a cavity in which the inner electrode of the first pair of electrodes and/or the inner electrode of the second pair of electrodes is electrically connected to a second one of the inner conductor and the outer conductor at the distal end of the coaxial transmission line. In this manner, the base structure may serve to protect the electrical connection between the inner electrode of the first pair and/or the second pair with the second one of the inner conductor and the outer conductor. The conductive material of the base structure may also serve to provide electromagnetic shielding for the electrical connection inside the cavity. The cavity may be a space or void defined within base structure.

The cavity may contain a dielectric material. This may ensure that the electrical connection in the cavity is electrically insulated, in order to avoid breakdown between the electrical connections inside the cavity and the surrounding base structure. The dielectric material may be any suitable type of dielectric material. As an example, an electrical potting material may be used as the dielectric material in the cavity, such as a thermosetting plastic, silicone, epoxy or resin.

The base structure may comprise an opening formed in a sidewall of the base structure for injecting a dielectric material into the cavity. For example, the opening may be a hole or aperture formed in the sidewall of the base structure. This may enable the dielectric material to be injected into the cavity, after assembly of the instrument tip at the distal end of the energy conveying structure. This may facilitate assembly of the instrument tip.

In some embodiments, the outer electrode of the first pair of electrodes and the outer electrode of the second pair of electrodes may both be electrically connected to a first one of the inner conductor and the outer conductor, and the inner electrode of the first pair of electrodes and the inner electrode of the second pair of electrodes are both electrically connected to a second one of the inner conductor and the outer conductor. Such a configuration of the electrodes may enable a first RF cutting field to be established between the first pair of electrodes, and a second RF cutting field to be established between the second pair of electrodes, thus enabling RF cutting of tissue to occur at both jaws. The two RF fields may be substantially symmetrical about the cutting interface between the blade elements, which may yield a highly uniform cut of tissue held between the jaws. Additionally, with such an electrode configuration, a substantially symmetrical microwave field may be emitted across the jaws, enabling microwave ablation and/or coagulation of tissue around the jaws.

An example of such an embodiment may be where there is a first conductive shell and a second conductive shell which are electrically coupled together and connected to a first one of the inner conductor and the outer conductor, and the inner electrodes of both pairs are connected to a second one of the inner conductor and outer conductor.

The inner electrode of the first pair of electrodes and the inner electrode of the second pair of electrodes may be in contact with one another, such that a sliding electrical contact is formed between them. Thus, the inner electrodes of the two pairs may be in physical contact with one another, such that they are in direct electrical contact with one another. The inner electrode of the first pair may be arranged to slide across the inner electrode of the second pair when the jaws are moved between the open and closed positions. The inner electrodes of the two pairs may be shaped such that portions of the inner electrodes remain in physical contact even when the jaws are in the open position. Such an electrical contact between the inner electrodes on each jaw may enable them to effectively act as a single larger electrode. This may also facilitate electrical connection between the energy conveying structure and the inner electrodes, as only one of the inner electrodes may need to be directly connected to the energy conveying structure.

As an example, the first electrode may be connected to a first connection pad located on the inner surface of the first planar dielectric element, the second electrode may be connected to a second connection pad located on the inner surface of the second planar dielectric element, and the first and second connection pads may be in contact with one another such that a sliding electrical contact is formed between them. The first connection pad and the second connection pad may be aligned with an axis about which the first and second jaws are pivotable relative to one another. This may ensure that the contact pads remain in contact as the jaws are pivoted relative to one another.

The first jaw may be fixed relative to the distal end of the energy conveying structure, and the second jaw may be movable relative to the distal end of the energy conveying structure; and the inner electrode of the first pair of electrodes may be electrically connected to one of the inner conductor and the outer conductor. Thus, the inner electrode on the movable jaw (i.e. the second jaw) may not need to be directly electrically connected to the energy conveying structure, as it is connected via its electrical contact with the inner electrode on the fixed jaw (i.e. the first jaw). This may simplify construction of the instrument tip, as well as improve a reliability of the electrical connection to the inner electrode on the movable jaw (e.g. as it is not connected via a wire that could break due to motion of the jaw). As an example, the first jaw may be rigidly mounted to the distal end of the energy conveying structure (e.g. via the first base part mentioned above), whilst the second jaw may be mounted so as to be pivotable relative to the first jaw (and thus relative to the distal end of the energy conveying structure).

In some embodiments, the outer electrode of the first pair of electrodes and the inner electrode of the second pair of electrodes may be connected to a first one of the inner conductor and the outer conductor; and the inner electrode of the first pair of electrodes and the outer electrode of the second pair of electrodes may be electrically connected to a second one of the inner conductor and the outer conductor. In other words, the inner electrodes of each pair may have opposing polarities, and the outer electrodes of each pair may have opposing polarities. Such a configuration of the electrodes may enable a first RF cutting field to be established between the first pair of electrodes, a second RF cutting field to be established between the second pair of electrodes, and a third RF cutting field to be established between the inner electrode of the first pair and the inner electrode of the second pair. As a result, RF cutting of tissue may occur at each jaw, as well as at the cutting interface between the first and second blade elements. Thus, RF cutting may be effected over an area corresponding to the jaws. Additionally, with such an electrode configuration, two separate microwave fields may be emitted: a first one by the first pair of electrodes, and a second one by the second pair of electrodes. This may improve a uniformity of microwave ablation and/or coagulation of tissue around the jaws.

The first jaw and/or second jaw may comprise a dielectric material arranged between the inner electrode of the first pair of electrodes and the inner electrode of the second pair of electrodes, to isolate them from one another. In some cases, the dielectric material may be disposed entirely on the first jaw or the second jaw. Alternatively, the dielectric material may be split between the two jaws, i.e. a first part of the dielectric material may be arranged on the first jaw, and a second part of the dielectric material may be arranged on the second jaw.

The dielectric material may be in the form of a planar dielectric element, and may have a shape that is similar to the first and/or second planar dielectric element. The dielectric material may be arranged to define all or part of one of the blade elements. For example, the dielectric material may comprise a cutting edge which is arranged to contact and cut tissue located between the jaws.

The instrument tip may be dimensioned to fit within an instrument channel of a surgical scoping device. Accordingly, in another aspect the invention provides an electrosurgical apparatus comprising: an electrosurgical generator for supplying radiofrequency (RF) electromagnetic (EM) energy and microwave EM energy; a surgical scoping device having an instrument cord for insertion into a patient's body, the instrument cord having an instrument channel extending therethrough; and an electrosurgical resector tool as described above inserted through the instrument channel of the surgical scoping device.

The apparatus may comprise a handpiece for controlling the electrosurgical resector tool. The handpiece may be mounted at a proximal end of the shaft, e.g. outside the surgical scoping device.

The term "surgical scoping device" may be used herein to mean any surgical device provided with an insertion tube that is a rigid or flexible (e.g. steerable) conduit that is introduced into a patient's body during an invasive procedure. The insertion tube may include the instrument channel and an optical channel (e.g. for transmitting light to illuminate and/or capture images of a treatment site at the distal end of the insertion tube. The instrument channel may have a diameter suitable for receiving invasive surgical tools. The diameter of the instrument channel may be 5 mm or less.

Herein, the term "inner" means radially closer to the centre (e.g. axis) of the instrument channel and/or coaxial transmission line. The term "outer" means radially further from the centre (axis) of the instrument channel and/or coaxial transmission line.

The term "conductive" is used herein to mean electrically conductive, unless the context dictates otherwise.

Herein, the terms "proximal" and "distal" refer to the ends of the elongate tool. In use the proximal end is closer to a generator for providing the RF and/or microwave energy, whereas the distal end is further from the generator.

In this specification "microwave" may be used broadly to indicate a frequency range of 400 MHz to 100 GHz, but preferably the range 1 GHz to 60 GHz. Specific frequencies that have been considered are: 915 MHz, 2.45 GHz, 3.3 GHz, 5.8 GHz, 10 GHz, 14.5 GHz and 24 GHz. In contrast, this specification uses "radiofrequency" or "RF" to indicate a frequency range that is at least three orders of magnitude lower, e.g. up to 300 MHz, preferably 10 kHz to 1 MHz, and most preferably 400 kHz.

BRIEF DESCRIPTION OF THE DRAWINGS

Embodiments of the invention are discussed in detail with reference to the accompanying drawings, in which.

DETAILED DESCRIPTION OF THE DRAWINGS

Figure 1:
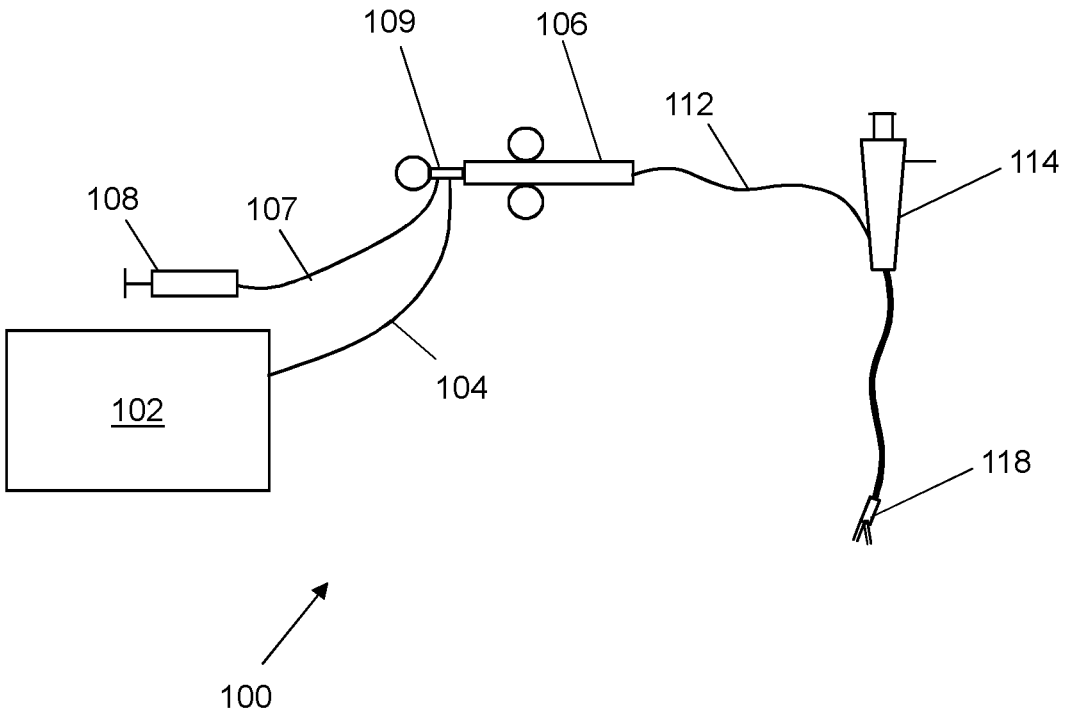
FIG. 1 is a schematic diagram of an electrosurgical system that is an embodiment of the invention.

FIG. 1 is a schematic diagram of a complete electrosurgical system 100 that is an embodiment of the invention. The system 100 is arranged to treat (e.g. cut or seal) biological tissue using radiofrequency (RF) or microwave electromagnetic (EM) energy from an instrument tip. The system 100 comprises a generator 102 for controllably supplying the RF and microwave EM energy. A suitable generator for this purpose is described in WO 2012/076844, which is incorporated herein by reference. The generator 102 is connected to a handpiece 106 by an interface cable 104. The handpiece 106 may also be connected to receive a fluid supply 107 from a fluid delivery device 108, such as a syringe, although this is not essential. If needed, the handpiece 106 may house an instrument actuation mechanism that is operable by an actuator 109, e.g. a thumb operated slider or plunger. For example the instrument actuation mechanism may be used to operate opening and closing of jaws of a resector instrument, as discussed herein. Other mechanisms may also be included in the handpiece. For example, a needle movement mechanism may be provided (operable by a suitable trigger on the handpiece) for deploying a needle at the instrument tip. A function of the handpiece 106 is to combine the inputs from the generator 102, fluid delivery device 108 and instrument actuation mechanism, together with any other inputs which may be required, into a single flexible shaft 112, which extends from the distal end of the handpiece 106.

The flexible shaft 112 is insertable through the entire length of an instrument (working) channel of a surgical scoping device 114. The flexible shaft 112 has an instrument tip 118 that is shaped to pass through the instrument channel of the surgical scoping device 114 and protrude (e.g. inside the patient) at the distal end of the endoscope's insertion tube. The instrument tip 118 includes a pair of jaws having blade elements for gripping and cutting biological tissue, and an energy delivery structure arranged to deliver RF or microwave EM energy conveyed from the generator 102. Optionally the instrument tip 118 may also include a retractable hypodermic needle for delivering fluid conveyed from the fluid delivery device 108. The handpiece 106 includes an actuation mechanism for opening and closing the jaws of the instrument tip 118. The handpiece 106 may also include a rotation mechanism for rotating the instrument tip 118 relative to the instrument channel of the surgical scoping device 114.

The structure of the instrument tip 118 may be arranged to have a maximum outer diameter suitable for passing through the working channel. Typically, the diameter of a working channel in a surgical scoping device such as an endoscope is less than 4.0 mm, e.g. any one of 2.8 mm, 3.2 mm, 3.7 mm, 3.8 mm. The flexible shaft 112 may have a maximum diameter less than this, e.g. 2.65 mm. The length of the flexible shaft 112 can be equal to or greater than 1.2 m, e.g. 2 m or more. In other examples, the instrument tip 118 may be mounted at the distal end of the flexible shaft 112 after the shaft has been inserted through the working channel (and before the instrument cord is introduced into the patient). Alternatively, the flexible shaft 112 can be inserted into the working channel from the distal end before making its proximal connections. In these arrangements, the distal end assembly 118 can be permitted to have dimensions greater than the working channel of the surgical scoping device 114. The system described above is one way of introducing the instrument into a patient. Other techniques are possible. For example, the instrument may also be inserted using a catheter.

Although the examples herein are present in the context of a surgical scoping device, it is to be understood that the electrosurgical resector instrument may be embodied in a device suitable for open surgery or use with a laparoscope.

Figure 2:
FIG. 2 is a schematic perspective view of an electrosurgical resector tool according to an embodiment of the invention.
Figure 2:
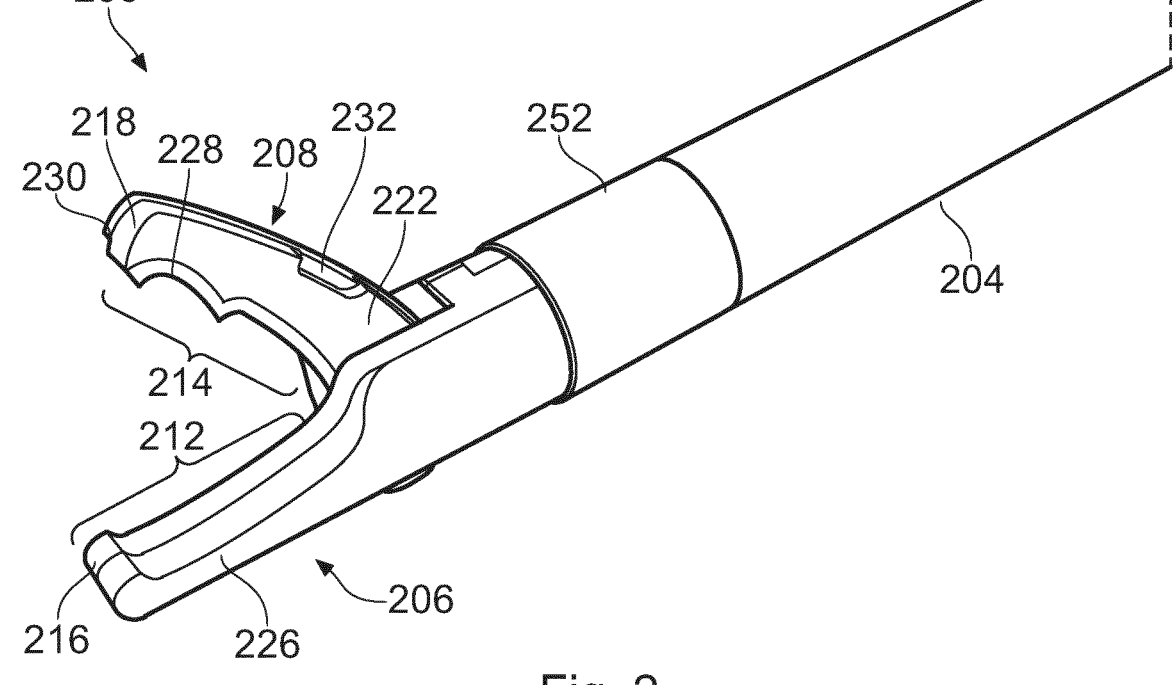
Figure 3:
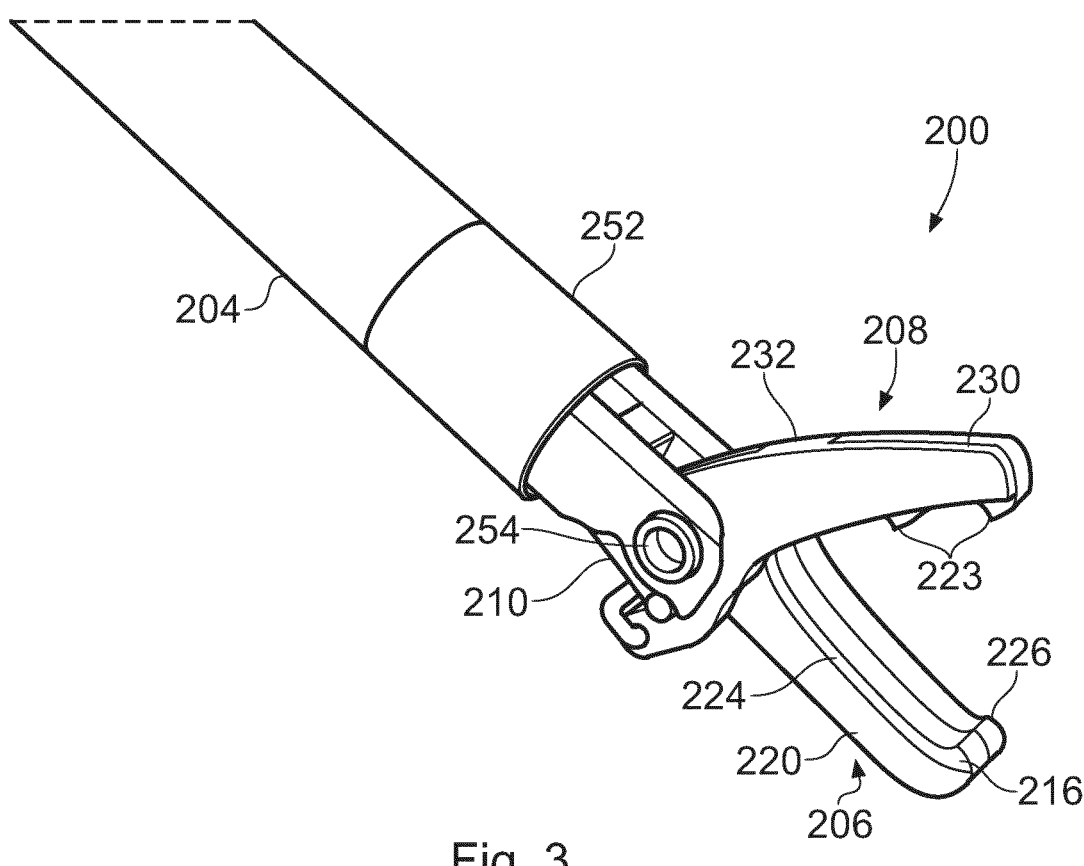
FIG. 3 is a schematic perspective view of the electrosurgical resector tool of FIG. 2.

FIGS. 2-8 illustrate an instrument tip 200 of an electrosurgical resector tool that is an embodiment of the invention. The instrument tip 200 may, for example, correspond to the instrument tip 118 discussed above in relation to FIG. 1. FIG. 2 shows a first schematic perspective view of the instrument tip 200, depicting a first side of the instrument tip 200, and FIG. 3 shows a second schematic perspective view of the instrument tip 200, depicting a second side of the instrument tip 200. FIGS. 4-8 illustrate a construction of the instrument tip 200.

The instrument tip 200 is mounted at a distal end of an energy conveying structure, which is in the form of a coaxial cable 202 (shown in FIGS. 4 and 6-8). The coaxial cable 202 extends through a flexible shaft 204, which may correspond to the flexible shaft 112 discussed above. In particular, the flexible shaft 204 defines a lumen through which the coaxial cable 202 extends, with the instrument tip 200 protruding from a distal end of the flexible shaft 204. The coaxial cable 202 is arranged to convey RF and microwave EM energy to the instrument tip 200 from an electrosurgical generator (e.g. generator 102 mentioned above).

The instrument tip 200 has a first jaw 206 and a second jaw 208 which are movable relative to one another between an open position and a closed position. Specifically, in the example shown, the first jaw 206 is static, i.e. it is fixed relative to the distal end of the coaxial cable 202, whilst the second jaw 208 is pivotally mounted to the first jaw 208. An actuator in the form of a control wire (or rod) 210 is connected to the second jaw 208 (see e.g. FIGS. 3 and 8), in order to control movement of the second jaw 208 relative to the first jaw 206. The control wire 210 disposed within the lumen of the flexible shaft 204, and is longitudinally slidable within the lumen to move the second jaw 208. A proximal end of the control wire 210 may be connected to a handpiece (e.g. handpiece 106), which is operable to control movement of the second jaw 208 via the control wire 210. FIGS. 2 and 3 depict the jaws 206, 208 in the open position, where a gap is defined between the jaws 206, 208 in which tissue can be received.

The first jaw 206 comprises a first blade element 212, and the second jaw 208 comprises a second blade element 214. Each blade element may comprise an edge which is arranged to contact tissue located in the gap between the jaws, and to cut the tissue when the jaws are moved to the closed position. Specifically, the second blade element 214 is arranged to slide across the first blade element 212 when the second jaw 208 is moved towards the closed position, such that a shearing force is applied to tissue located in the gap between the jaws 206, 208. Thus, tissue located in the gap between the jaws can be cut by pivoting the second jaw 208 towards the closed position.

The first blade element 212 is defined by a first planar dielectric element 216 in the first jaw 206, and the second blade element 214 is defined by a second planar dielectric element 218 in the second jaw 208. In particular, the first planar dielectric element 216 includes an inner surface 220 that faces towards the second planar dielectric element 218, and across which an inner surface 222 of the second planar dielectric element 218 slides when the second jaw 208 is pivoted relative to the first jaw 206, such that there is a shearing motion between the two planar dielectric elements. Each of the first and second planar dielectric elements may be made from ceramic (e.g. alumina) or other suitable electrically insulating material. The first and second planar dielectric elements each define a plane which is parallel to a plan through which the second jaw 208 pivots relative to the first jaw 206. The second planar dielectric element 218 includes a pair of projections (or teeth) 223, which act as serrations for the second blade element 214. Thus, the projections 223 may serve to grip tissue located in the gap between the jaws, to facilitate holding and/or cutting the tissue. The first planar dielectric element 216 may include similar projections (not shown), to act as serrations for the first blade element 212.

The instrument tip 200 further includes two pairs of electrodes, one located on each jaw. The first jaw 206 includes an inner electrode 224 formed on the inner surface 220 of the first planar dielectric element 216, and an outer electrode 226 arranged on an outer surface of the first planar dielectric element 216. Similarly, the second jaw 206 includes an inner electrode 228 formed on the inner surface 222 of the second planar dielectric element 218, and an outer electrode 230 arranged on an outer surface of the second planar dielectric element 218. Thus, the first planar dielectric element 216 serves to electrically isolate the inner and outer electrodes of the first jaw 206 from one another, whilst the second planar dielectric element 218 serves to electrically isolate the inner and outer electrodes of the second jaw 208 from one another.

The inner electrode 224 of the first jaw 206 is formed by a layer or film of conductive material (e.g. gold), which is deposited on the inner surface 220 of the first planar dielectric element 216. The inner electrode 224 covers part of the inner surface 220, and extends along a cutting edge of the first blade element 212 (i.e. of the first planar dielectric element 216), such that it is located at a cutting interface between the first and second blade elements when the jaws are closed. The outer electrode 226 of the first jaw 206 is in the form of a first conductive shell which is attached (e.g. glued) to the outer surface of the first planar dielectric element 216. The first conductive shell, is a piece of conductive material which covers the entire outer surface of the first planar dielectric element 216, and which has a thickness that is similar to a thickness of the first planar dielectric element 216. An outer surface of the first conductive shell acts an outer surface of the first jaw 206. The outer surface of the first conductive shell may be rounded, so that the first jaw 206 has a smooth outer surface.

The electrodes of the second jaw 208 are formed in a similar manner to those of the first jaw 206. In particular, the inner electrode 228 of the second jaw 208 is formed by a layer or film of conductive material (e.g. gold), which is deposited on the inner surface 222 of the second planar dielectric element 218. The inner electrode 228 covers part of the inner surface 222, and extends along a cutting edge of the second blade element 214 (i.e. of the second planar dielectric element 218), such that it is located at the cutting interface between the first and second blade elements when the jaws are closed. The outer electrode 230 of the second jaw 208 is in the form of a second conductive shell which is attached (e.g. glued) to the outer surface of the second planar dielectric element 218. The second conductive shell, is a piece of conductive material which covers a majority of the outer surface of the second planar dielectric element 218, and which has a thickness that is similar to a thickness of the second planar dielectric element 218. An outer surface of the second conductive shell forms an outer surface of the second jaw 206. As shown in FIG. 2, the second conductive shell has a protrusion 232 which is engaged in a groove in the second planar dielectric element 218. Engagement of the protrusion 232 in the groove serves to align the second conductive shell with the second planar dielectric element 218, and avoid slippages between the two parts. Of course, different types of engagement features for locating the second conductive shell relative to the second planar dielectric element 218 may be used. Similar engagement features may also be used for locating the first conductive shell relative to the first planar dielectric element 216.

The pair of electrodes on each jaw is electrically connected to the distal end of the coaxial cable 202, so that the electrodes can deliver RF and microwave EM energy conveyed by the coaxial cable 202. The manner in which the electrodes are connected to the coaxial cable is discussed in more detail below.

A construction of the instrument tip 200 is now discussed with reference to FIGS. 4-8, which depict various stages of assembly of the instrument tip 200. The coaxial cable 202 includes an inner conductor 234 and an outer conductor 236 which are separated by a dielectric material 238. Additionally, the coaxial cable 202 includes an outer sheath 240 which is made of an insulating material. The first jaw 206 and the second jaw 208 are mounted to the distal end of the coaxial cable 202 via a base structure 242. The base structure 242 includes a first base part 244 made of a conductive material, which rigidly connects the first jaw 206 to the distal end of the coaxial cable 202. The first base part 244 comprises an arm which extends between the distal end of the coaxial cable 202 and the first conductive shell (which forms the outer electrode 226 of the first jaw 206). In the example shown, the first conductive shell and the first base part 244 are integrally formed as a single piece of conductive material. However, in other examples, they may be formed as separate parts that are connected together. The first base part 244 includes a first mounting portion 246 that includes a channel in which the distal end of the coaxial cable 202 is received. A length of the outer sheath 240 of the coaxial cable 202 is removed in the vicinity of the distal end of the coaxial cable, so that the outer conductor 236 is exposed. The outer conductor 236 is thus in electrical contact with the first base part 244 in the channel in the first mounting portion 246. The distal end of the coaxial cable 202 may be secured in the channel in the first mounting portion 246 using a suitable conductive epoxy. As a result, the first conductive shell (and thus the outer electrode 226 of the first jaw 206) is electrically connected to the outer conductor 236 via the first base part 244.

Figure 8:
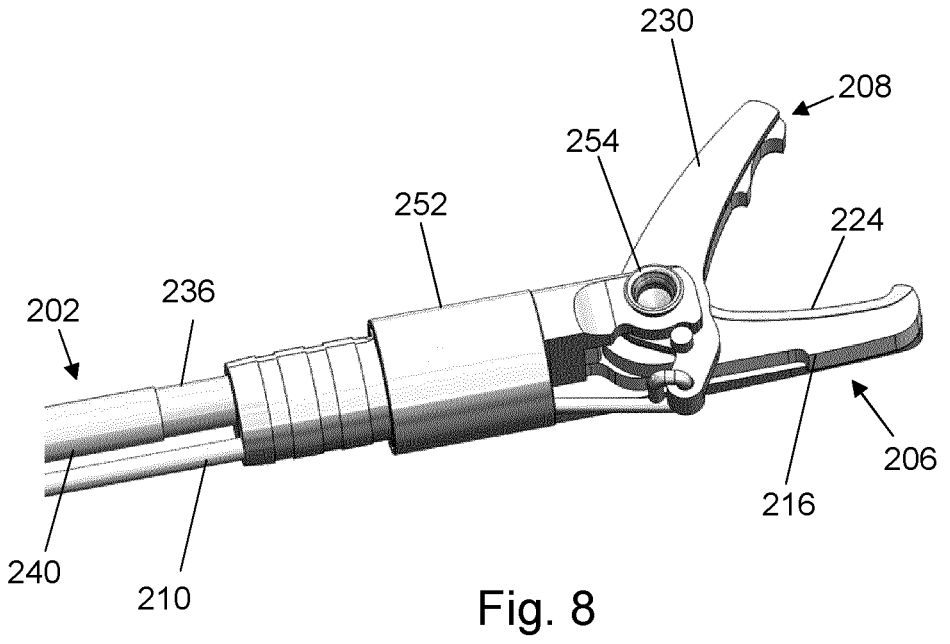
FIG. 8 is a schematic diagram of the electrosurgical resector tool of FIG. 2, prior to complete assembly.

The base structure 242 further comprises a second base part 248, which pivotably mounts the second jaw 208 to the distal end of the coaxial cable 202. The second base part 248 is made of a conductive material, which may be the same material as the first base part 244 (e.g. stainless steel). The second base part 248 includes a second mounting portion 250 which is secured to the first mounting portion 246 on the first base part 244, such that the first base part 244 and the second base part 248 are in electrical contact. The first mounting portion 246 and the second mounting portion 250 have complimentarily shaped engagement surfaces which are engaged with one another when the base parts are secured together. As shown in FIG. 8, the first base part 244 and the second base part 248 are secured together via a conductive ring 252 that fits around the first and second mounting portions 246, 250 to hold them together. An adhesive may be injected inside the conductive ring 252, in order to secure the conductive ring 252 in place over the first and second mounting portions. In addition to holding the base structure 242 together, the conductive ring 252 may act as a microwave shield, which prevents microwave energy from being radiated prior to reaching the electrodes in the jaws.

The second base part 248 includes an arm that extends longitudinally from the second mounting portion 250, and to which the second conductive shell (which forms the outer electrode 230 on the second jaw 208) is pivotably mounted. In the example shown, the second conductive shell is pivotably mounted to the second base part 240 via a rivet 254. The second conductive shell is in electrical contact with the second base part 248 via the rivet 254 (which is made of a conductive material). Thus, the second conductive shell (and hence the outer electrode 230 on the second jaw 208) is electrically connected to the outer conductor 236 of the coaxial cable 202. Accordingly, both the outer electrode 226 of the first jaw 206 and the outer electrode 230 of the second jaw are electrically connected to the outer conductor 236 via the base structure 242.

Figure 6:
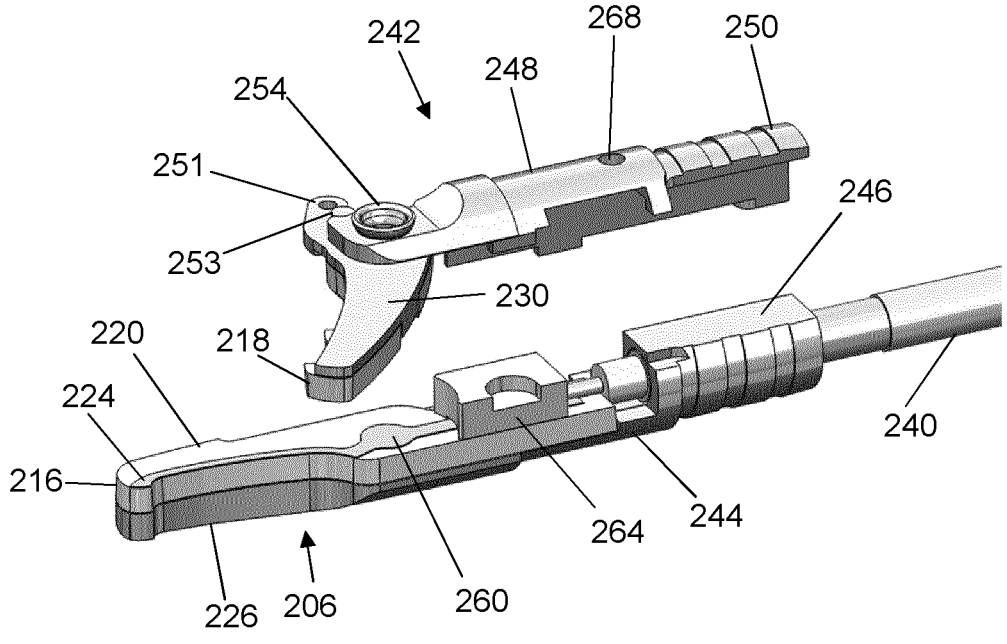
FIG. 6 is a schematic diagram depicting parts of the electrosurgical resector tool of FIG. 2 prior to assembly.

As shown in FIG. 6, the second base part 248 may include a passageway 249 through which the control wire 210 extends to connect to the second jaw 208. The second conductive shell may include an attachment portion 251, to which a distal end of the control wire 210 is connected. The second conductive shell may also be provided with a limiting pin 253 (shown in FIG. 6), which serves to limit motion of the second jaw 208 relative to the first jaw 206 between the open and closed positions. This may enable the position of the second jaw 208 to be controlled more accurately.

Figure 4:
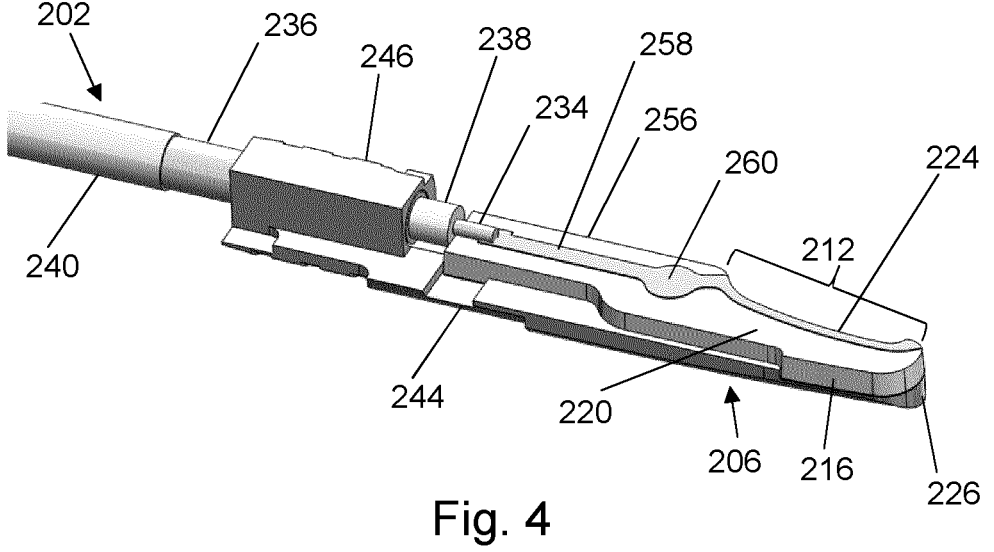
FIG. 4 is a schematic diagram depicting part of the electrosurgical resector tool of FIG. 2.

The inner electrode 224 of the first jaw 206 is electrically connected to the inner conductor 234 of the coaxial cable 202. As shown in FIG. 4, the first planar dielectric element 216 includes a connecting portion 256 which extends between the first blade element 212 and the distal end of the coaxial cable 202. A distal end of the inner conductor 234 protrudes beyond the distal end of the coaxial cable 202 such that it lies on the connecting portion 256 of the first planar dielectric element 216. A wire 258 extends longitudinally along the connecting portion 256 of the first planar dielectric element, to electrically connect the inner electrode 224 to the distal end of the inner conductor 234. The wire 258 may be a part of the inner electrode 224 which extends along the connecting portion 256, e.g. the wire 258 and inner electrode 224 may be deposited together on the inner surface 220 of the first planar dielectric element 216.

The wire 258 comprises a first connection pad 260 (shown in FIGS. 4 and 5) formed on the inner surface 220 of the first planar dielectric element 216. The first connection pad 260 is arranged to contact a second connection pad 262 (shown in FIG. 6) formed on the inner surface 222 of the second planar dielectric element 218, such that a sliding electrical contact is formed between the first and second connection pads 260, 262. In particular, the first and second connection pads are centred about an axis of the rivet 254, about which the second jaw 208 pivots. Thus, the second connection pad 262 remains in electrical contact with the first connection pad 260, as the second jaw 208 pivots relative to the first jaw 206. The second connection pad 262 is electrically connected to the inner electrode 228 of the second jaw 208. For example, the second connection pad 262 may be part of the inner electrode 228, and/or may be deposited on the inner surface 222 together with the inner electrode 228. In this manner, the inner electrode 228 of the second jaw 208 is electrically connected to the inner conductor 234, via the connection pads 260, 262 and the wire 258.

Figure 7:
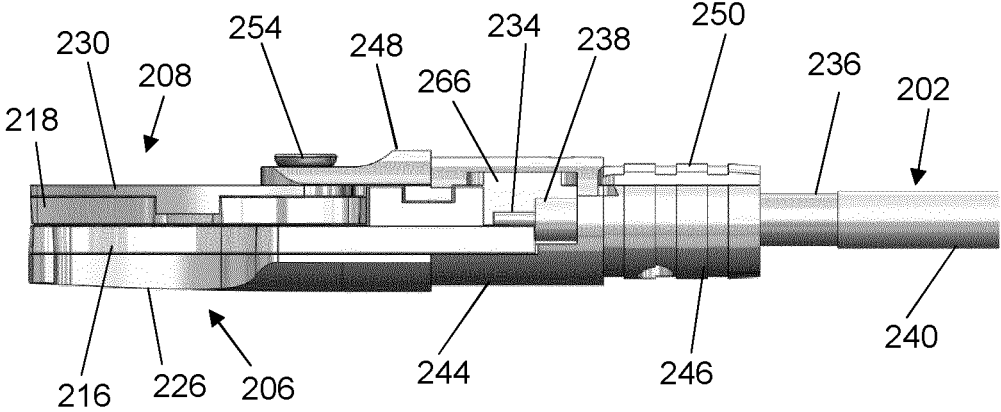
FIG. 7 is a schematic diagram of the electrosurgical resector tool of FIG. 2, prior to complete assembly.

A dielectric block 264 is mounted between the second base part 248 and the first planar dielectric element 216, in order to avoid electrical breakdown between the wire 258 and the conductive second base part 248. For example, the dielectric block 264 may be made of a ceramic material, such as alumina. The dielectric block 264 may be secured in place using an adhesive. Further, as shown in FIG. 7, the base structure 242 is shaped such that a cavity 266 is formed between the first base part 244 and the second base part 248, in which the inner conductor 234 is electrically connected to the wire 258 (and thus to the inner electrodes 224, 228). The cavity 266 may be filled with a dielectric material, such as a potting material, in order to reduce the risk of electrical breakdown between the distal end of the inner conductor 234 and the base structure 242. Filling the cavity 266 with a dielectric material may also serve to reinforce the instrument tip 200, and hold the first and second base parts together. The second base part 248 includes an injection port 268 via which dielectric material can be injected into the cavity 266.

Figure 5:
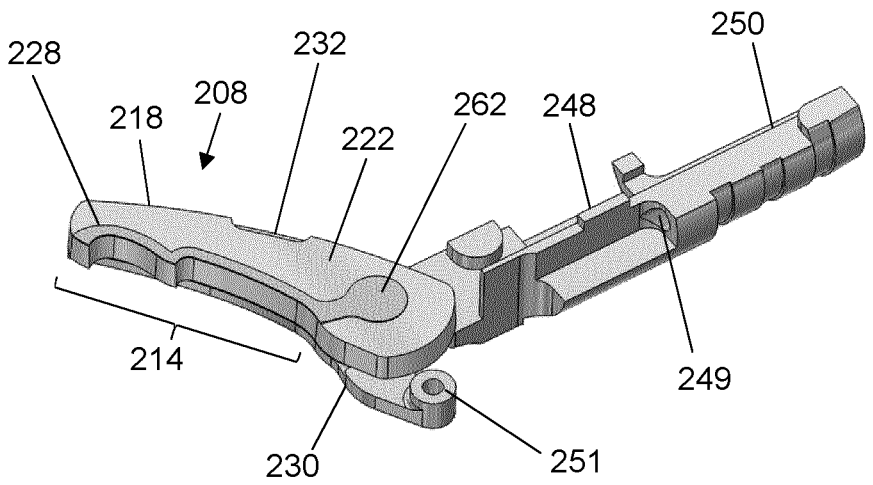
FIG. 5 is a schematic diagram depicting part of the electrosurgical resector tool of FIG. 2.

To assemble the instrument tip 200, the first base part 244 and first jaw 208 may first be assembled and connected to the distal end of the coaxial cable 202 as shown in FIG. 4. As shown in FIGS. 5 and 6, the second jaw 208 is connected to the second base part 248 via the rivet 254. Then, the dielectric block 264 may be placed on the inner surface 220 of the first planar dielectric element 216 (as shown in FIG. 6), following which second base part 248 is mounted on the first base part 244 (as shown in FIG. 7). A dielectric potting material may then be injected into the cavity 266, via the injection port 268. The conductive ring 252 may then be slid over the coaxial cable 202 and onto the first and second mounting portions 246, 250, to hold the first and second base parts 244, 248 together. As noted above, an adhesive may be used to secure the conductive ring 252 over the first and second mounting portions 246, 250. The control wire 210 may then be threaded through the passageway 249 in the second base part 248, and connected to the attachment portion on the second jaw 208 (as shown in FIG. 8). Finally, the flexible shaft 204 may be pulled over the coaxial cable 202, and secured to the conductive ring 252, e.g. using an adhesive.

In the embodiment described with reference to FIGS. 2-8, only one of the jaws is movable. However, in other embodiments, both jaws may be movably mounted to the distal end of the coaxial cable 202, e.g. to provide a scissor-like opening and closing of the jaws. It should also be noted that different electrical connections to the electrodes may be used in different embodiments. For instance, in some embodiments, the inner electrodes could be connected to the outer conductor 236, whilst the outer electrodes could be connected to the inner conductor. Various electrode configurations are discussed below with reference to FIGS. 9 and 10.

Figure 9:
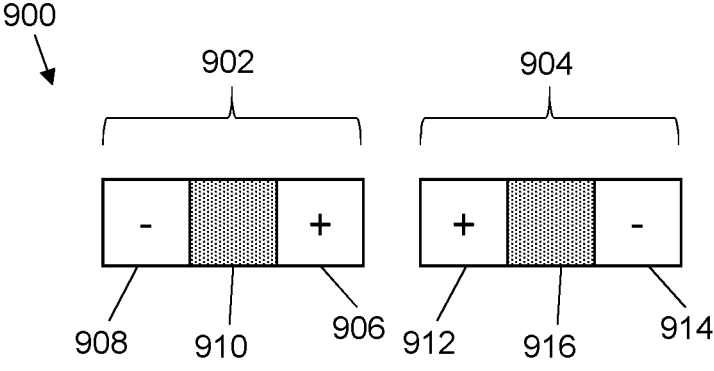
FIG. 9 is a schematic diagram illustrating an instrument tip of an electrosurgical resector tool according to an embodiment of the invention.
Figure 10:
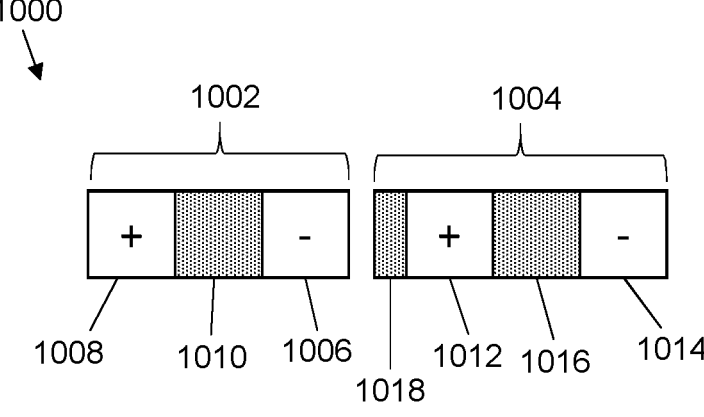
FIG. 10 is a schematic diagram illustrating an instrument tip of an electrosurgical resector tool according to an embodiment of the invention.

FIGS. 9 and 10 are schematic diagrams illustrating possible electrode configurations in an electrosurgical resector tool according to embodiments of the invention.

FIG. 9 shows a schematic cross-sectional diagram of part of an instrument tip 900 of an electrosurgical resector tool, having a first jaw 902 and a second jaw 904. The first and second jaws are movable (e.g. pivotable) relative to one another, and each include a respective blade element for cutting tissue located between the jaws. The first jaw 902 includes a first inner electrode 906 and a first outer electrode 908 which are separated by a first dielectric material 910. The first inner electrode 906 is electrically connected to an inner conductor of a coaxial cable of the electrosurgical resector tool, whilst the first outer electrode 908 is electrically connected to an outer conductor of the coaxial cable. Similarly, the second jaw 904 includes a second inner electrode 912 and a second outer electrode 914 which are separated by a second dielectric material 916. The second inner electrode 912 is electrically connected to the inner conductor of the coaxial cable, whilst the second outer electrode 914 is electrically connected to the outer conductor of the coaxial cable. The '+' and '−' signs in FIGS. 9-10 indicate which of the inner and outer conductor of the coaxial cable each electrode is connected to, with '+' indicating that the electrode is connected to the inner conductor and '−' indicating that the electrode is connected to the outer conductor.

Thus, the electrode configuration shown in FIG. 9 may correspond to that of instrument tip 200 discussed above, where the inner electrodes are connected to the inner conductor of the coaxial cable, and the outer electrodes are connected to the outer conductor of the coaxial cable. So, for example, the first inner electrode 906 may correspond to the inner electrode 224, the first outer electrode 908 may correspond to the outer electrode 226, the first dielectric material 910 may correspond to the first planar dielectric element 216, the second inner electrode 912 may correspond to the inner electrode 228, the second outer electrode 914 may correspond to the outer electrode 230, and the second dielectric material 916 may correspond to the second planar dielectric element 218. Thus, there may be a sliding electrical contact (not shown) between the first inner conductor 906 and the second inner conductor 912.

With the electrode configuration shown in FIG. 9, two RF cutting fields may be generated when RF EM energy is conveyed to the electrodes via the coaxial cable. A first RF cutting field may be established between the first inner electrode 906 and the first outer electrode 908, with the first inner electrode 906 acting as a first active electrode and the first outer electrode 908 acting as a first return electrode for the RF EM energy. Likewise, a second RF cutting field may be established between the second inner electrode 912 and the second outer electrode 914, with the second inner electrode 912 acting as a second active electrode and the second outer electrode 914 acting as a second return electrode for the RF EM energy. As a result, the RF cutting fields may be substantially symmetrical about an interface between the two jaws, which may enable uniform RF cutting of tissue. Additionally, with the embodiment of instrument tip 200 discussed above, where the outer electrodes are formed by large conductive shells whilst the inner electrodes are formed by thin layers of conductive material, RF cutting may be focused near the inner electrodes. This is because RF cutting of tissue tends to occur at the smaller of the two electrodes. Accordingly, by making the outer electrodes 908,914 larger (e.g. by providing them with a larger surface area) than the inner electrodes 906, 912, RF cutting of tissue may be focused at the interface between the first and second jaws 902, 904, which may yield a fine and accurate cut.

When microwave EM energy is delivered to the electrodes in jaws 902, 904 via the coaxial cable, a microwave field may be established around the jaws. In particular, the inner electrodes and outer electrodes may together act as a microwave field emitting structure (or antenna structure) for emitting the microwave energy. As the first inner electrode 906 and the second inner electrode 912 are electrically connected together, they may act as a single microwave emitter for emitting the microwave energy. The first outer electrode 908 and the second outer electrode 914 may act as grounded conductors which shape the emitted microwave energy. Such a microwave field emitting structure may result in a substantially symmetrical microwave field being emitted around the jaws. With the embodiment of instrument tip 200, as the outer conductors are provided by conductive shells on the outer surfaces of the jaws, the emitted microwave energy may be focused around the jaws and in the gap between the jaws. This may ensure that microwave ablation and/or coagulation of tissue occurs in a well-defined region around the jaws.

Of course, in other embodiments, the polarities of the electrodes may be reversed compared to those shown in FIG. 9. For example, in some embodiments, the first inner electrode 906 may be connected to the outer conductor, the first outer electrode 908 may be connected to the inner conductor, the second inner electrode 912 may be connected to the outer conductor, and the second outer electrode 914 may be connected to the inner conductor.

FIG. 10 shows a schematic cross-sectional diagram of part of an instrument tip 1000 of an electrosurgical resector tool, having a first jaw 1002 and a second jaw 1004. The first and second jaws are movable (e.g. pivotable) relative to one another, and each include a respective blade element for cutting tissue located between the jaws. The first jaw 1002 includes a first inner electrode 1006 and a first outer electrode 1008 which are separated by a first dielectric material 1010. The first inner electrode 1006 is electrically connected to an outer conductor of a coaxial cable of the electrosurgical resector tool, whilst the first outer electrode 1008 is electrically connected to an inner conductor of the coaxial cable. Similarly, the second jaw 1004 includes a second inner electrode 1012 and a second outer electrode 1014 which are separated by a second dielectric material 1016. The second inner electrode 1012 is electrically connected to the outer conductor of the coaxial cable, whilst the second outer electrode 1014 is electrically connected to the inner conductor of the coaxial cable. Thus, the inner electrodes of the two jaws are connected to opposite conductors in the coaxial cable, and the outer electrodes of the two jaws are connected to opposite conductors in the coaxial cable.

In order to prevent electrical connection between the first inner electrode 1006 and the second inner electrode 1012, the second jaw 1004 includes a third dielectric material 1018 which covers the second inner electrode 1012, and which is located between the second inner electrode 1012 and the first inner electrode 1006. The third dielectric material 1018 may be made of the same dielectric material as the first and second dielectric materials 1010, 1016 and may, for example, be in the form of a planar dielectric element which is mounted in the second jaw 1004. The third dielectric material 1018 may serve to define the blade element of the second jaw 1004, e.g. the third dielectric material 1018 may have a cutting edge which is arranged to cut tissue located between the jaws. The third dielectric element 1018 may also serve to protect the second inner electrode 1018. Additionally or alternatively, a fourth piece of dielectric material (not shown) may be provided on the first jaw 1002, such that it covers the first inner electrode 1006 and is located between the first inner electrode 1006 and the second inner electrode 1012. The fourth piece of dielectric material may serve to define the blade element of the first jaw 1002. Covering each of the first and second inner conductors with a dielectric material in this manner may minimise a risk of electrical breakdown between the inner electrodes. This may also improve a symmetry between the jaws, which may in turn improve a symmetry of the RF and microwave energy emitted by the instrument tip.

With the electrode configuration shown in FIG. 10, three RF cutting fields may be generated when RF EM energy is conveyed to the electrodes via the coaxial cable. A first RF cutting field may be established between the first inner electrode 1006 and the first outer electrode 1008, with the first inner electrode 1006 acting as a first return electrode and the first outer electrode 1008 acting as a first active electrode for the RF EM energy. A second RF cutting field may be established between the second inner electrode 1012 and the second outer electrode 1014, with the second inner electrode 1012 acting as a second active electrode and the second outer electrode 1014 acting as a second return electrode for the RF EM energy. Additionally, a third RF cutting field may be established between the first inner electrode 1006 and the second inner electrode 1012, as they are connected to different conductors in the coaxial cable. As a result, an RF cutting field may be established at each jaw, as well as between the jaws. This may improve a uniformity with which RF cutting of tissue located between the jaws can be performed, as well as enable RF cutting to be performed across a larger area of the jaws. Similarly to the discussion above, the RF cutting may be focused at an interface between the jaws 1002, 1004, by increasing a size of the outer electrodes 1008, 1014 relative to the inner electrodes 1006, 1012. For example, the outer electrodes 1008, 1014 may be implemented by relatively larger conductive shells on the outer surfaces of the jaws, whilst the inner electrodes 1006, 1012 may be implemented by thin conductive layers in the jaws.

When microwave energy is delivered to the electrodes in jaws 1002, 1004, a respective microwave field may be emitted by the pair of electrodes in each jaw. In particular, the first inner electrode 1006 and the first outer electrode 1008 may act as a first microwave field emitting structure, whilst the second inner electrode 1012 and the second outer electrode 1014 may act as a second microwave field emitting structure. As a result, a respective microwave field may be emitted at each jaw. This may enable tissue located between the jaws to be treated with microwave energy substantially symmetrically about an interface between the jaws. For instance, this may enable tissue located between the jaws to be ablated and/or coagulated substantially uniformly on either side.

Of course, in other embodiments, the polarities of the electrodes may be reversed compared to those shown in FIG. 10. For example, in some embodiments, the first inner electrode 1006 may be connected to the inner conductor, the first outer electrode 1008 may be connected to the outer conductor, the second inner electrode 1012 may be connected to the outer conductor, and the second outer electrode 1014 may be connected to the inner conductor.

It should be noted that the parts of the instrument tips depicted in FIGS. 9 and 10 are not shown to scale. Additionally, for illustration purposes, FIGS. 9 and 10 do not show the first and second jaws as touching. However, in practice, the first and second jaws may be in contact with one another, e.g. they may be pivotably connected together.

The invention claimed is:

1. An electrosurgical instrument comprising:
an energy conveying structure for carrying radiofrequency (RF) electromagnetic (EM) energy and microwave EM energy, the energy conveying structure comprising a coaxial transmission line having an inner conductor separated from an outer conductor by a dielectric material;
an instrument tip mounted at a distal end of the energy conveying structure, wherein the instrument tip comprises a first jaw and a second jaw;

wherein the second jaw is movable relative to the first jaw between a closed position in which the first jaw and the second jaw lie alongside each other, and an open position in which the second jaw is spaced from the first jaw by a gap for receiving biological tissue;
wherein the first jaw comprises a first pair of electrodes that are electrically isolated from one another;
wherein the second jaw comprises a second pair of electrodes that are electrically isolated from one another;
wherein the first pair of electrodes is coupled to the energy conveying structure, such that the first pair of electrodes is operable as active and return electrodes for delivering RF EM energy carried by the energy conveying structure;
wherein the second pair of electrodes is coupled to the energy conveying structure, such that the second pair of electrodes is operable as active and return electrodes for delivering RF EM energy carried by the energy conveying structure;
wherein the first and second pairs of electrodes are operable as a microwave field emitting structure for emitting microwave EM energy carried by the energy conveying structure;
wherein the instrument tip further comprises a base structure that connects the first jaw and the second jaw to the distal end of the energy conveying structure;
wherein the base structure includes a first base part that rigidly connects the first jaw to the distal end of the energy conveying structure, and a second base part to which the second jaw is pivotably connected, such that the second jaw is pivotable relative to the second base part;
wherein the first base part comprises a first mounting portion comprising a channel in which the distal end of the energy conveying structure is received;
wherein the second base part comprises a second mounting portion; and
wherein the first base part and the second base part are secured together via a conductive ring that fits around the first mounting portion and second mounting portions to hold them together.

2. The electrosurgical instrument according to claim 1, wherein:
the first jaw comprises a first planar dielectric element having an inner surface that faces towards the second jaw and an outer surface that faces away from the second jaw, and the first pair of electrodes comprises an inner electrode and an outer electrode arranged on the inner and outer surfaces of the first planar dielectric element, respectively; and
the second jaw comprises a second planar dielectric element having an inner surface that faces towards the first jaw and an outer surface that faces away from the first jaw, and the second pair of electrodes comprises an inner electrode and an outer electrode arranged on the inner and outer surfaces of the second planar dielectric element, respectively.

3. The electrosurgical instrument according to claim 2, wherein:
the inner electrode of the first pair of electrodes comprises a first conductive layer formed on the inner surface of the first planar dielectric element; and
the inner electrode of the second pair of electrodes comprises a second conductive layer formed on the inner surface of the second planar dielectric element.

4. The electrosurgical instrument according to claim 2, wherein:

the first jaw further comprises a first conductive shell that is attached to the outer surface of the first planar dielectric element, and arranged to form at least part of the outer electrode of the first pair of electrodes; and the second jaw further comprises a second conductive shell that is attached to the outer surface of the second planar dielectric element, and arranged to form at least part of the outer electrode of the second pair of electrodes.

5. The electrosurgical instrument according to claim 4, wherein the first conductive shell and the second conductive shell are electrically coupled to one another.

6. The electrosurgical instrument according to claim 4, wherein the base structure comprises an electrically conductive material that electrically connects the first conductive shell or the second conductive shell to a first one of the inner conductor and the outer conductor at a distal end of the coaxial transmission line.

7. The electrosurgical instrument according to claim 6, wherein the base structure defines a cavity in which the inner electrode of the first pair of electrodes or the inner electrode of the second pair of electrodes is electrically connected to a second one of the inner conductor and the outer conductor at the distal end of the coaxial transmission line.

8. The electrosurgical instrument according to claim 7, wherein the cavity contains a dielectric material.

9. The electrosurgical instrument according to claim 7, wherein the base structure comprises an opening formed in a sidewall of the base structure for injecting a dielectric material into the cavity.

10. The electrosurgical instrument according to claim 2, wherein the outer electrode of the first pair of electrodes and the outer electrode of the second pair of electrodes are both electrically connected to a first one of the inner conductor and the outer conductor, and the inner electrode of the first pair of electrodes and the inner electrode of the second pair of electrodes are both electrically connected to a second one of the inner conductor and the outer conductor.

11. The electrosurgical instrument according to claim 10, wherein the inner electrode of the first pair of electrodes and the inner electrode of the second pair of electrodes are in contact with one another, such that a sliding electrical contact is formed between them.

12. The electrosurgical instrument according to claim 11, wherein:

the first jaw is fixed relative to the distal end of the energy conveying structure, and the second jaw is movable relative to the distal end of the energy conveying structure; and the inner electrode of the first pair of electrodes is electrically connected to one of the inner conductor and the outer conductor.

13. The electrosurgical instrument according to claim 2, wherein:

the outer electrode of the first pair of electrodes and the inner electrode of the second pair of electrodes are connected to a first one of the inner conductor and the outer conductor; and the inner electrode of the first pair of electrodes and the outer electrode of the second pair of electrodes are electrically connected to a second one of the inner conductor and the outer conductor.

14. The electrosurgical instrument according to claim 13, wherein the first jaw or second jaw comprises a dielectric material arranged between the inner electrode of the first pair of electrodes and the inner electrode of the second pair of electrodes, to isolate them from one another.

15. An electrosurgical apparatus comprising:

an electrosurgical generator for supplying radiofrequency (RF) electromagnetic (EM) energy and microwave EM energy;

a surgical scoping device having an instrument cord for insertion into a patient's body, the instrument cord having an instrument channel extending therethrough; and the electrosurgical instrument according to claim 1 inserted through the instrument channel of the surgical scoping device.

16. An electrosurgical resector tool comprising:

an energy conveying structure for carrying radiofrequency (RF) electromagnetic (EM) energy and microwave EM energy, the energy conveying structure comprising a coaxial transmission line having an inner conductor separated from an outer conductor by a dielectric material;

an instrument tip mounted at a distal end of the energy conveying structure, wherein the instrument tip comprises a first jaw and a second jaw;

wherein the second jaw is movable relative to the first jaw between a closed position in which the first jaw and the second jaw lie alongside each other, and an open position in which the second jaw is spaced from the first jaw by a gap for receiving biological tissue;

wherein the first jaw comprises a first pair of electrodes that are electrically isolated from one another;

wherein the second jaw comprises a second pair of electrodes that are electrically isolated from one another;

wherein the first pair of electrodes is coupled to the energy conveying structure, such that the first pair of electrodes is operable as active and return electrodes for delivering RF EM energy carried by the energy conveying structure;

wherein the second pair of electrodes is coupled to the energy conveying structure, such that the second pair of electrodes is operable as active and return electrodes for delivering RF EM energy carried by the energy conveying structure;

wherein the first and second pairs of electrodes are operable as a microwave field emitting structure for emitting microwave EM energy carried by the energy conveying structure;

wherein the first jaw comprises a first planar dielectric element having an inner surface that faces towards the second jaw and an outer surface that faces away from the second jaw, and the first pair of electrodes comprises an inner electrode and an outer electrode arranged on the inner and outer surfaces of the first planar dielectric element, respectively;

the second jaw comprises a second planar dielectric element having an inner surface that faces towards the first jaw and an outer surface that faces away from the first jaw, and the second pair of electrodes comprises an inner electrode and an outer electrode arranged on the inner and outer surfaces of the second planar dielectric element, respectively;

wherein the instrument tip further comprises a base structure that connects the outer electrodes of the first pair of electrode and the outer electrode of the second pair of electrodes to the distal end of the energy conveying structure;

wherein the base structure comprises an electrically conductive material that forms a first electrical connection from:

the outer electrode of the first pair of electrodes or the outer electrode of the second pair of electrodes; to a first one of the inner conductor and the outer conductor at a distal end of the coaxial transmission line;

wherein the base structure defines a cavity in which the inner electrode of the first pair of electrodes or the inner electrode of the second pair of electrodes forms a second electrical connection to a second one of the inner conductor and the outer conductor at the distal end of the coaxial transmission line; and wherein the cavity contains a solid dielectric material that electrically insulates the first electrical connection from the second electrical connection.

*     *     *     *     *